(12) United States Patent
Walsh et al.

(10) Patent No.: US 7,651,526 B2
(45) Date of Patent: Jan. 26, 2010

(54) VASCULAR GRAFT

(75) Inventors: Michael Thomas Walsh, County Limerick (IE); Timothy M. McGloughlin, County Limerick (IE); Pierce Grace, County Limerick (IE)

(73) Assignee: University of Limerick, Limerick (IE)

( * ) Notice: Subject to any disclaimer, the term of this patent is extended or adjusted under 35 U.S.C. 154(b) by 571 days.

(21) Appl. No.: 11/331,275

(22) Filed: Jan. 13, 2006

(65) Prior Publication Data

US 2006/0116753 A1   Jun. 1, 2006

Related U.S. Application Data

(63) Continuation of application No. PCT/IE2004/000094, filed on Jul. 8, 2004.

(60) Provisional application No. 60/486,443, filed on Jul. 14, 2003.

(51) Int. Cl.
    *A61F 2/06* (2006.01)
(52) U.S. Cl. .................................................. 623/1.35
(58) Field of Classification Search ............... 623/1.35, 623/1.13, 1.14, 1.23, 1.25; 606/153, 154, 606/155

See application file for complete search history.

(56) References Cited

U.S. PATENT DOCUMENTS

| | | | | |
|---|---|---|---|---|
| 2,127,903 A | * | 8/1938 | Bowen | 606/154 |
| 4,501,263 A | * | 2/1985 | Harbuck | 128/898 |
| 5,197,976 A | | 3/1993 | Herweck et al. | 623/1 |
| 6,315,752 B1 | * | 11/2001 | DiMatteo | 604/8 |
| 6,416,542 B1 | * | 7/2002 | Marcade et al. | 623/1.16 |
| 6,585,762 B1 | * | 7/2003 | Stanish | 623/1.3 |
| 6,599,302 B2 | * | 7/2003 | Houser et al. | 606/153 |
| 6,746,480 B2 | * | 6/2004 | Scholz et al. | 623/1.31 |
| 2003/0088256 A1 | * | 5/2003 | Conston et al. | 606/155 |
| 2003/0125797 A1 | * | 7/2003 | Chobotov et al. | 623/1.13 |
| 2004/0215125 A1 | * | 10/2004 | Brown | 604/6.16 |
| 2006/0167539 A1 | * | 7/2006 | McEwan | 623/1.35 |
| 2006/0229709 A1 | * | 10/2006 | Morris et al. | 623/1.31 |
| 2006/0229710 A1 | * | 10/2006 | O'Brien et al. | 623/1.35 |
| 2007/0118208 A1 | * | 5/2007 | Kerr | 623/1.13 |
| 2008/0081965 A1 | * | 4/2008 | Edman et al. | 600/309 |
| 2008/0103587 A1 | * | 5/2008 | Henderson et al. | 623/1.35 |

FOREIGN PATENT DOCUMENTS

| | | |
|---|---|---|
| EP | 0137605 | 4/1985 |
| FR | 2666502 | 3/1992 |
| WO | WO00/48531 | 8/2000 |

* cited by examiner

*Primary Examiner*—Anhtuan T Nguyen
*Assistant Examiner*—Sarah A Simpson
(74) *Attorney, Agent, or Firm*—Jacobson Holman PLLC (57) ABSTRACT

A vascular graft includes a proximal section, integral with two branches which terminate in a distal end-to-end section. The end-to-end section is attached to a host artery at end-to-end anastomoses. Flow of blood from the proximal section to the host artery occurs with a self-correcting flow pattern at the opposing junctions, avoiding arterial bed impingement and associated risk of restenosis.

21 Claims, 9 Drawing Sheets

VASCULAR GRAFT

This is a continuation of PCT/IE04/000094 filed Jul. 8, 2004 and published in English, claiming benefit of U.S. provisional application No. 60/486,443, filed Jul. 14, 2003.

INTRODUCTION

This invention relates to a vascular graft and to a method of performing a vascular bypass procedure.

Figure 1:
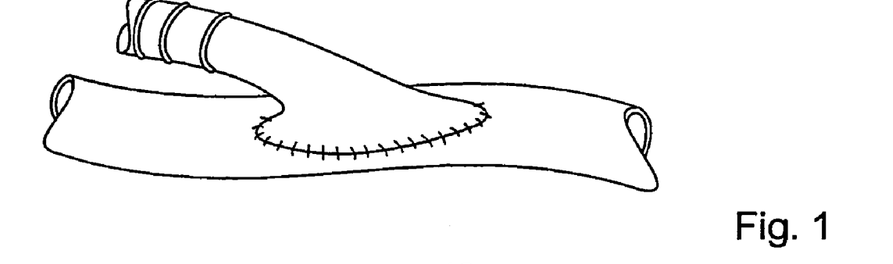
FIG. 1 is a schematic illustration of a conventional vascular graft, in use.

It is known to achieve the restoration of blood supply to ischemic limb extremities by using a vascular bypass graft, and this enables normal limb function to be maintained. A typical conventional vascular graft is illustrated in FIG. 1.

However, conventional vascular bypass procedures have moderate long term patency rates, typically between 33% and 41% at 60 months. Restenosis frequently occurs at the distal anastomosis, forming often on the artery bed opposite to the anastomosis. One major cause of restenosis is the initiation of intimal hyperplasia at this location. Disease formation on the artery bed opposite to the junction is believed to occur due to the abnormal flow patterns created as the flow exits the graft and enters the artery, impinging on the bed of the junction. The flow patterns created by the end-to-side distal anastomosis has been found to exert an abnormal wall shear stress distribution on the endothelial cells on the bed of the junction. In particular, flow impinging on the arterial bed creates a stagnation point. A stagnation point is associated with a low wall shear stress region as by definition the wall shear stress at the stagnation point is zero. However with flow impinging on the arterial bed a region of high wall shear stress is also created. Considering the low and high wall shear stress regions together, though they are at different locations on the bed of the junction, a significant wall shear stress gradient is clearly present. Since the flow is pulsatile in nature, the flow impinging on the arterial bed produces an oscillating stagnation point.

Figure 2:
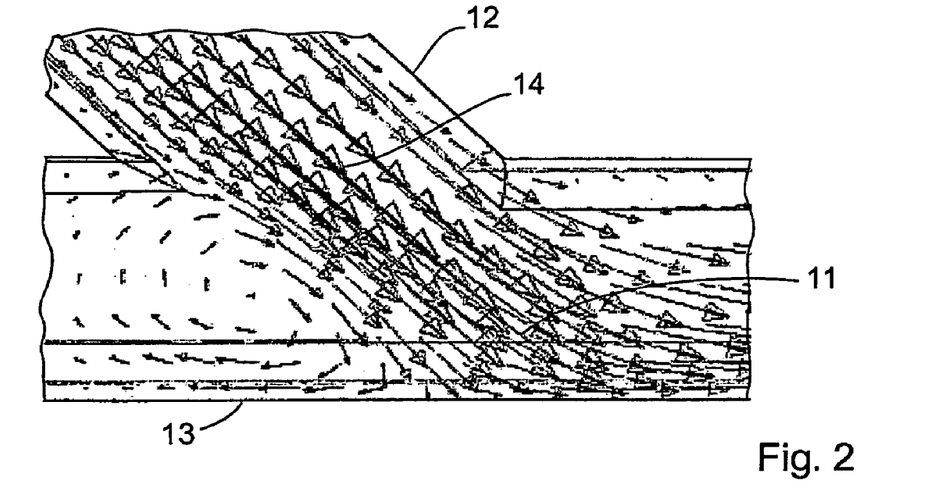
FIGS. 2 and 3 are cross-sectional, schematic illustrations of the graft of FIG. 1, in use.
Figure 3:
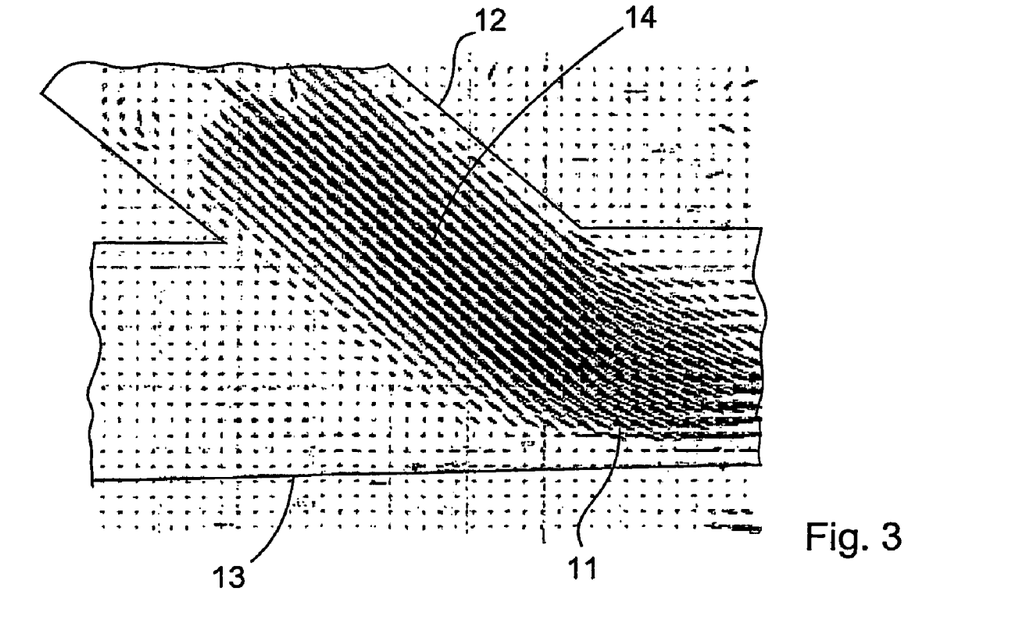

A typical flow pattern created using a conventional vascular graft is illustrated in FIGS. 2 and 3. FIG. 2 is a computational fluid dynamics (CFD) illustration of the flow pattern at an end-to-side idealised anastomosis. FIG. 3 shows the corresponding experimental flow visualisation results for the flow pattern in the same geometry using particle imaging velocimetry (PIV). In each illustration, the flow 14 exits from the conventional vascular graft 12 impinges on the artery 13 at a region 11 opposite to the junction of the graft 12 with the artery 13.

Conventional vascular grafts suffer from the problem that the flow exiting from the graft impinges on the junction bed, which often results in the initiation of disease formation.

This invention is therefore aimed at providing a vascular graft which overcomes at least some of the problems of conventional vascular grafts.

STATEMENTS OF INVENTION

According to the invention there is provided a vascular graft comprising:
  a first branch for directing flow between a first vasculature part and a second vasculature part along a first flow path; and
  a second branch for directing flow between the first vasculature part and the second vasculature part along a second flow path.

In one embodiment of the invention the graft is configured to discharge flow out of the first branch to impinge upon flow being discharged out of the second branch. By discharging the flow out of the first branch to impinge upon the flow being discharged out of the second branch, this results in the flow impingement occurring at a central region of the lumen away from the interior walls. In particular the flow exiting from the first branch impinges upon the flow exiting from the second branch, and as a result prevents the second branch flow from impinging on the interior wall. In a similar manner, the second branch flow impinges upon the first branch flow, and as a result prevents the first branch flow from impinging on the interior wall. By preventing the flow from impinging on the interior wall, the possibility of disease formation is minimised.

Preferably each branch comprises a distal opening through which flow is discharged out of the branch; and the distal opening of the first branch and the distal opening of the second branch are arranged opposing one another. The opposed distal openings ensure that the first branch flow effectively impinges upon the second branch flow. Ideally the distal opening of the first branch and the distal opening of the second branch are arranged diametrically opposing one another. Most preferably the distal opening of the first branch faces towards the distal opening of the second branch. By arranging for the distal openings to face towards one another, this arrangement provides for enhanced impingement of the first branch flow upon the second branch flow.

In another embodiment the branch comprises means to attach a distal end of the branch directly to a side wall of the second vasculature part. Preferably the distal opening of the first branch and the distal opening of the second branch are configured to be located at substantially the same longitudinal region along the length of the second vasculature part. When the distal openings are located at the same longitudinal region, the impingement of the first branch flow upon the second branch flow is optimised.

In a further embodiment the graft comprises a distal flow conduit for directing flow from the first branch and from the second branch to the second vasculature part. Preferably the distal flow conduit comprises means to attach a distal end of the distal flow conduit directly to a proximal end of the second vasculature part. Ideally the distal opening of the first branch and the distal opening of the second branch are located at substantially the same longitudinal region along the length of the distal flow conduit. When the distal openings are located at the same longitudinal region, the impingement of the first branch flow upon the second branch flow is optimised. Most preferably a distal end of the branch is connected to a side wall of the distal flow conduit. The first branch and the second branch may be connected to the distal flow conduit in a bifurcation arrangement.

The anastomotic angle defined between the branch and the distal flow conduit may be in the range of from 15° to 60°. The out-of-plane angle defined between the branch and the distal flow conduit may be in the range of from 5° to 45°.

In a preferred case the distal flow conduit extends distally of the distal end of the first branch and distally of the distal end of the second branch by at least 5 mm. Ideally the distal flow conduit extends proximally of the distal end of the first branch and proximally of the distal end of the second branch by at least 5 mm.

In one embodiment the distal flow conduit comprises means to attach a proximal end of the distal flow conduit to a third vasculature part. The third vasculature part may be an upstream part of a vascular vessel, and the second vasculature part may be a downstream part of the same vascular vessel. The third vasculature part may be an upstream part of a vascular vessel, and the second vasculature part may be a downstream part of a different vascular vessel.

Ideally the branch is integral with the distal flow conduit.

In one case the graft comprises a proximal flow conduit for directing flow from the first vasculature part to the first branch and to the second branch. Preferably the proximal flow conduit comprises means to attach a proximal end of the proximal flow conduit to the first vasculature part. Ideally the first branch and the second branch are connected to the proximal flow conduit in a bifurcation arrangement. The branch may be integral with the proximal flow conduit.

In another embodiment the graft comprises stiffening ribs around its circumference. The stiffening ribs enhance the structural rigidity of the graft to maximise flow through the branches. Preferably the ribs are not provided adjacent the distal end and/or adjacent the proximal end of the distal flow conduit.

The graft may be at least partially of a natural tissue material, such as harvested or grown vasculature materials. The graft may be at least partially of an artificial biomaterial, such as Dacron or ePTFE. The graft may be at least partially of a tissue engineered biomaterial.

In one case the first vasculature part is an upstream part of a vascular vessel, and the second vasculature part is a downstream part of the same vascular vessel. In another case the first vasculature part is an upstream part of a vascular vessel, and the second vasculature part in a downstream part of a different vascular vessel.

In another aspect of the invention there is provided a method of performing a vascular bypass procedure comprising the steps of:
  directing flow between a first vasculature part and a second vasculature part along a first flow path; and
  directing flow between the first vasculature part and the second vasculature part along a second flow path.

In one embodiment the flow is directed between the first vasculature part and the second vasculature part along the first flow path through a first branch of a vascular graft, and the flow is directed between the first vasculature part and the second vasculature part along the second flow path through a second branch of a different vascular graft. In another embodiment the flow is directed between the first vasculature part and the second vasculature part along the first flow path through a first branch of a vascular graft, and the flow is directed between the first vasculature part and the second vasculature part along the second flow path through a second branch of the same vascular graft.

Preferably flow is discharged out of the first branch to impinge upon flow being discharged out of the second branch.

In one case the method comprises the step of attaching a distal end of the branch directly to a side wall of the second vasculature part. Preferably the distal end of the first branch and the distal end of the second branch are attached to opposite sides of the second vasculature part. Ideally the distal end of the first branch and the distal end of the second branch are attached to the second vasculature part at substantially the same longitudinal region along the length of the second vasculature part.

In another case the method comprises the step of attaching a distal end of the vascular graft directly to a proximal end of the second vasculature part.

The method may comprise the step of attaching a proximal end of the vascular graft to the first vasculature part.

In one embodiment the method comprises the step of attaching a proximally extending portion of the vascular graft to a third vasculature part. The third vasculature part may be an upstream part of a vascular vessel, and the second vasculature part may be a downstream part of the same vascular vessel. The third vasculature part may be an upstream part of a vascular vessel, and the second vasculature part may be a downstream part of a different vascular vessel.

In one case the method comprises the step of forming the vascular graft at least partially from a natural tissue material. In another case the method comprises the step of forming the vascular graft at least partially from an artificial biomaterial. In a further case the method comprises the step of forming the vascular graft at least partially from a tissue engineered biomaterial.

The first vasculature part may be an upstream part of a vascular vessel, and the second vasculature part may be a downstream part of the same vascular vessel. The first vasculature part may be an upstream part of a vascular vessel, and the second vasculature part may be a downstream part of a different vascular vessel.

BRIEF DESCRIPTION OF THE DRAWINGS

The invention will be more clearly understood from the following description of some embodiments thereof, given by way of example only, with reference to the accompanying drawings, in which:—

FIGS. 15(a) to 17 are cross-sectional, schematic illustrations of the graft of FIG. 11, in use.

DETAILED DESCRIPTION

Referring to the drawings, and initially to FIGS. 4 to 10 thereof, there is illustrated a vascular graft 1 according to the invention for directing blood flow between a first vasculature part and a second vasculature part 5.

The first vasculature part and the second vasculature part 5 may be parts of the same vascular vessel. In such a case, the graft 1 directs blood flow from an upstream part of a vascular vessel to a downstream part of the same vascular vessel.

Alternatively the first vasculature part and the second vasculature part 5 may be parts of different vascular vessels. In such a case, the graft 1 directs blood flow from an upstream part of one vascular vessel to a downstream part of a different vascular vessel.

The graft 1 comprises a proximal flow conduit 4 for directing blood flow from the first vasculature part to a first branch 2 and to a second branch 3. The first branch 2 directs the blood flow from the proximal flow conduit 4 to the second vasculature part 5 along a first flow path through the first branch 2, and the second branch 3 directs the blood flow from the proximal flow conduit 4 to the second vasculature part 5 along a second flow path through the second branch 3.

The proximal flow conduit 4 comprises means to attach a proximal end of the proximal flow conduit 4 to the first vasculature part. The attachment means may be provided in the form of sutures.

The two branches 2, 3 are connected to a distal end of the proximal flow conduit 4 in a bifurcation arrangement (FIG. 4), with the graft 1 splitting from the single proximal flow conduit 4 into two outflow segments provided by the branches 2, 3. In this case the branches 2, 3 are provided integral with the proximal flow conduit 4.

Each branch 2, 3 comprises means to attach a distal end of the branch 2, 3 directly to a side wall of the second vasculature part 5 in the form of two end-to-side anastomoses. The attachment means may be provided in the form of sutures.

Figure 5:
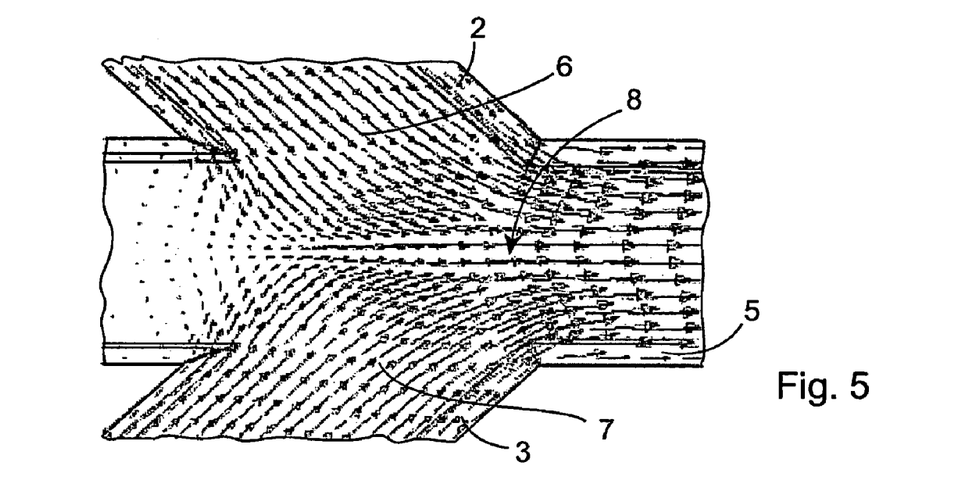
FIGS. 5 to 9 are cross-sectional, schematic illustrations of the graft of FIG. 4, in use.

Each branch 2, 3 has a distal opening 6, 7 through which blood flow is discharged out of the branch 2, 3 and into the second vasculature part 5 (FIG. 5). The branches 2, 3 are attached to the second vasculature part 5 with the distal openings 6, 7 arranged diametrically opposing one another, facing towards one another, and located at the same longitudinal region along the length of the second vasculature part 5.

By arranging the distal openings 6, 7 in this manner, the blood flow discharged out of the first branch 2 impinges upon the blood flow discharged out of the second branch 3. Because the first branch blood flow and the second branch blood flow impinge upon one another at a central region 8 of the lumen of the second vasculature part 5, the blood flow does not impinge on the inner wall of the second vasculature part 5. As a result the possibility of disease formation along the inner wall of the second vasculature part 5 is minimised. This aspect of the invention is illustrated in FIGS. 5 to 10.

Figure 6:
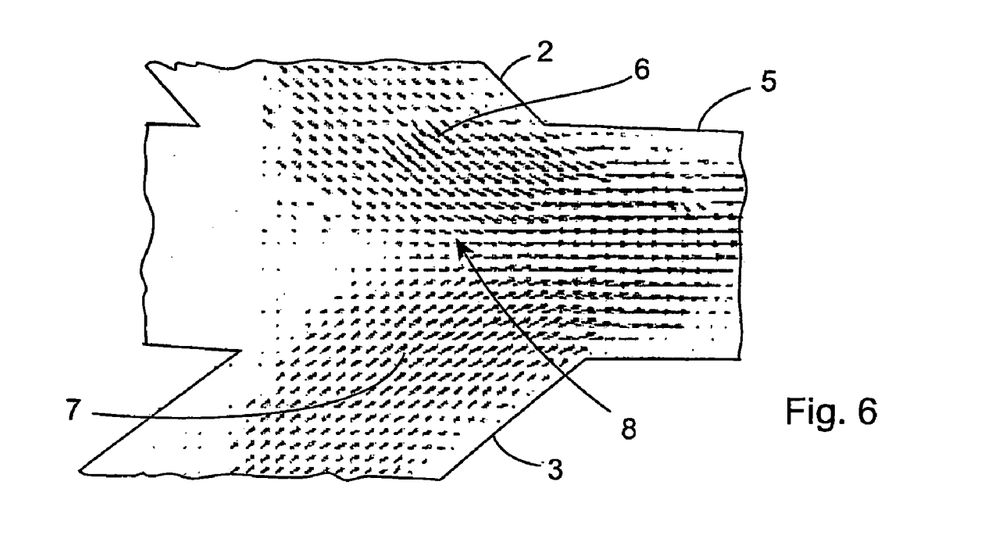
Figure 7:
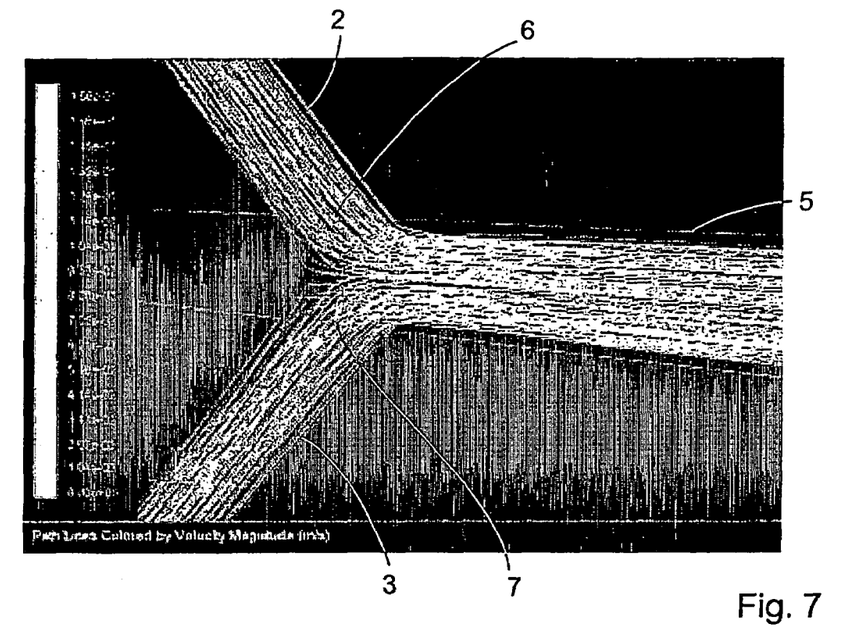
Figure 8:
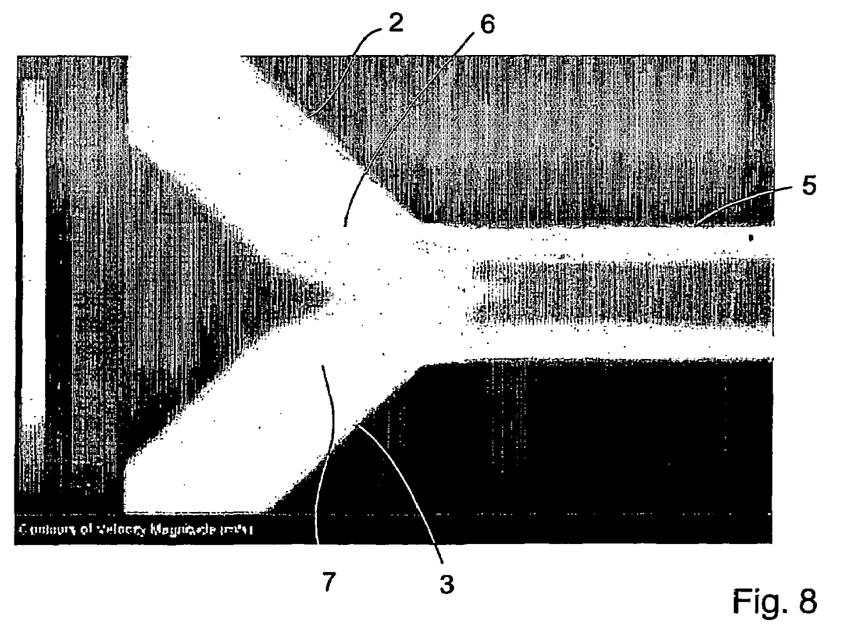
Figure 9:
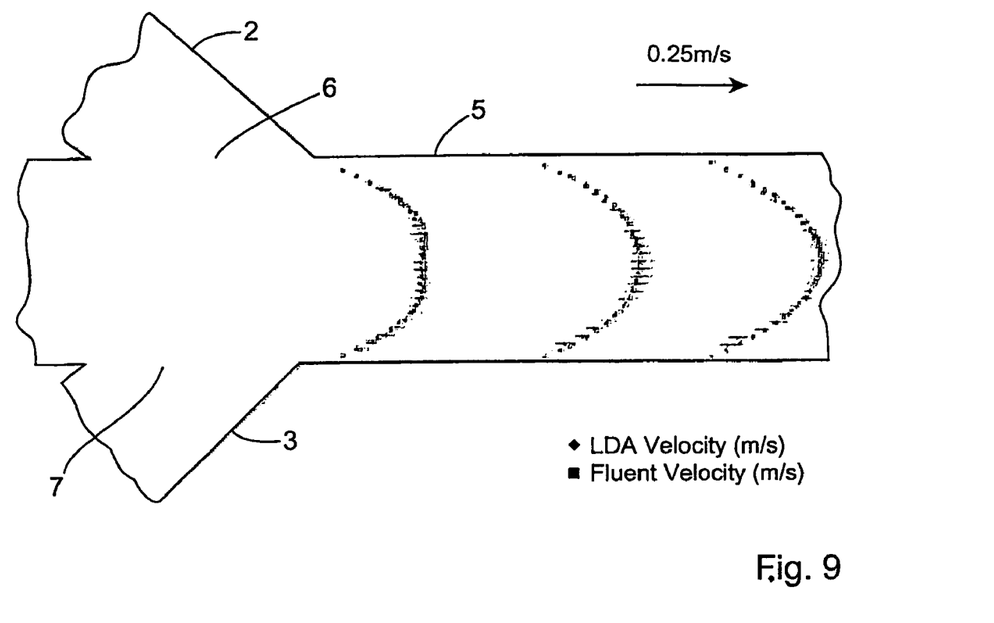

FIG. 5 illustrates, using computational flow dynamics (CFD), the flow patterns in the region of the distal openings 6, 7. FIG. 6 illustrates, using Particle Imaging Velocimetry studies, the flow patterns in the region of the distal openings 6, 7. The self-correcting nature of the flow in the central region 8 can be seen from FIGS. 5 and 6 also. FIG. 7 illustrates the path lines of the flow patterns in the region of the distal openings 6, 7. FIG. 8 illustrates the velocity contours of the flow patterns in the region of the distal openings 6, 7. FIG. 9 illustrates, using laser doppler anemometry (LDA) results and corresponding CFD results, the flow patterns in the region of the distal openings 6, 7.

Figure 10:
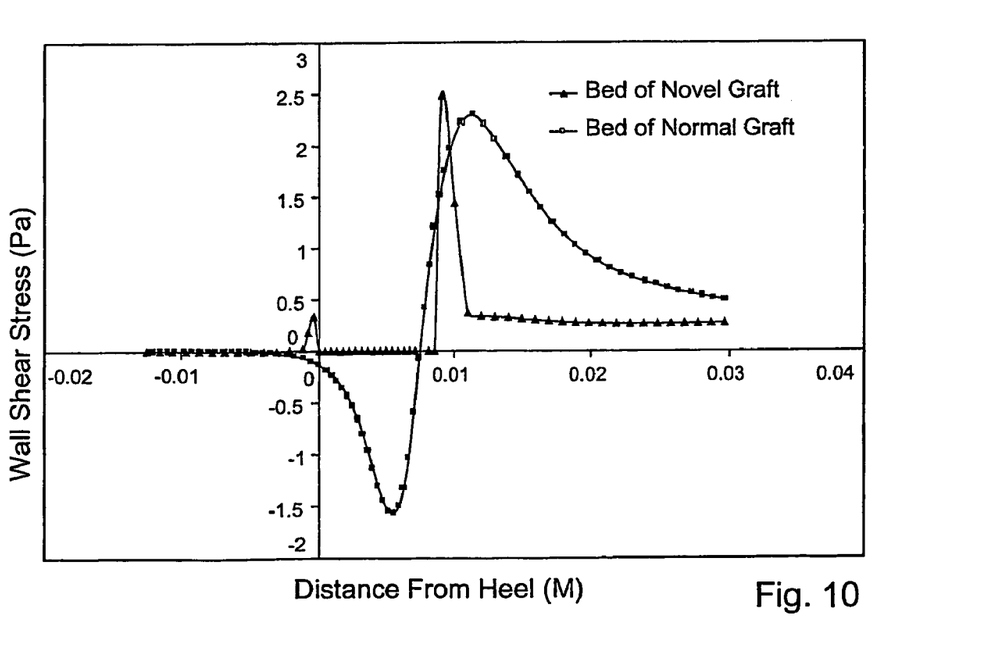
FIG. 10 is a graph illustrating wall shear stress distribution for the graft of FIG. 1 and for the graft of FIG. 4.

FIG. 10 is a graph illustrating wall shear stress distribution along the inner wall of the vasculature part 5 in the region of the distal openings 6, 7 using the vascular graft 1 of the invention (FIG. 5), and wall shear stress distribution at the region 11 opposite to the junction of the conventional vascular graft 12 with the artery 13 (FIG. 2).

The graft 1 may be employed when performing a vascular bypass procedure between the first vasculature part and the second vasculature part 5. In use, a proximal end of the proximal flow conduit 4 is attached to the first vasculature part, for example by means of suturing. The distal ends of the branches 2, 3 are directly attached to opposite sides of the side wall of the second vasculature part 5 in the form of two end-to-side anastomoses, for example by means of suturing. The branches 2, 3 are attached with the distal openings 6, 7 arranged diametrically opposing one another, facing towards one another, and located at the same longitudinal region along the length of the second vasculature part 5.

In this manner, blood flow is directed from the first vasculature part into the proximal flow conduit 4, from the proximal flow conduit 4 into the first branch 2 and into the second branch 3, through the first branch 2 along the first flow path and through the second branch 3 along the second flow path, from the first branch 2 and from the second branch 3 into the second vasculature part 5. The blood flow discharged out of the first branch 2 impinges upon the blood flow discharged out of the second branch 3.

It will be appreciated that the vascular bypass procedure could alternatively be performed using two conventional vascular grafts. In this case the first flow path is provided through one graft, and the second flow path is provided through the other graft. By attaching the distal ends of the two conventional grafts to the side wall of the second vasculature part 5 with the distal openings opposing one another, facing towards one another, and located at the same longitudinal region along the length of the second vasculature part 5, the blood flow discharged out of each graft impinges on one another.

Figure 4:
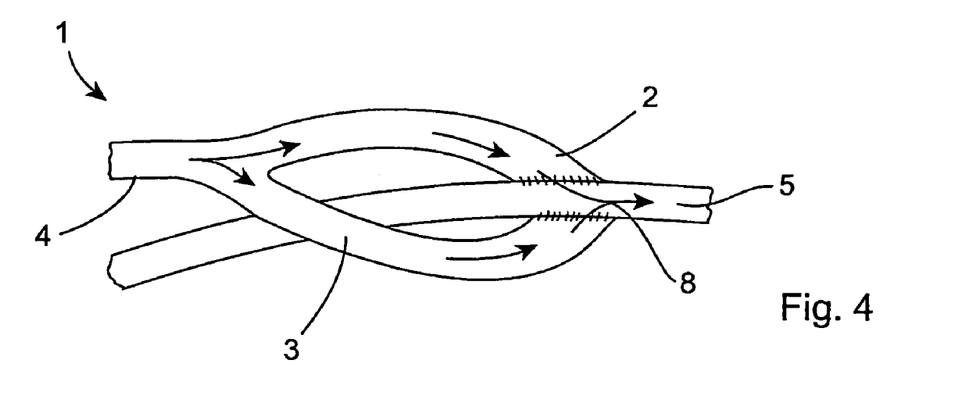
FIG. 4 is a schematic illustration of a vascular graft according to the invention, in use.

Referring to FIG. 4 the bypass graft 1 of the invention has two outflow branch sections 2, 3 at the end of the proximal primary section 4 (which may be of any suitable length). These are attached to the artery 5 using end-to-side surgical techniques. However, because they are attached at opposing locations there is no arterial bed and therefore no site for initiation of disease formation.

Because the graft 1 of the invention has opposed side branches 2, 3 for inflow to the host artery there is a self-correcting flow pattern. This is shown in FIGS. 5 to 9.

While the graft system described above with reference to FIGS. 4 to 10 has very favourable flow characteristics, the surgical procedures required may be difficult in some circumstances. For example it may difficult to gain access to a suitable portion of a side wall of the second vasculature part 5 to attach the distal end of the branch thereto. This may be especially so, when it is desired to gain access to an underside of the second vasculature part 5.

Figure 11:
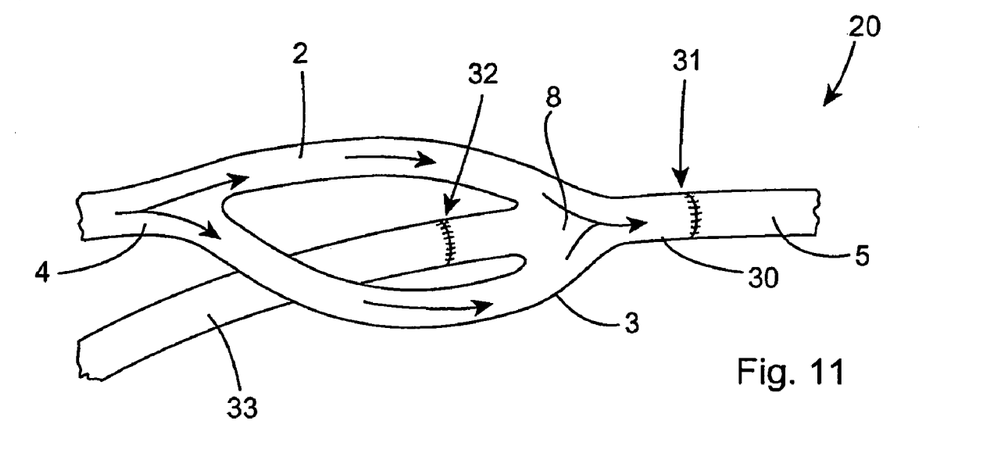
FIG. 11 is a schematic illustration of another vascular graft according to the invention, in use.
Figure 12:
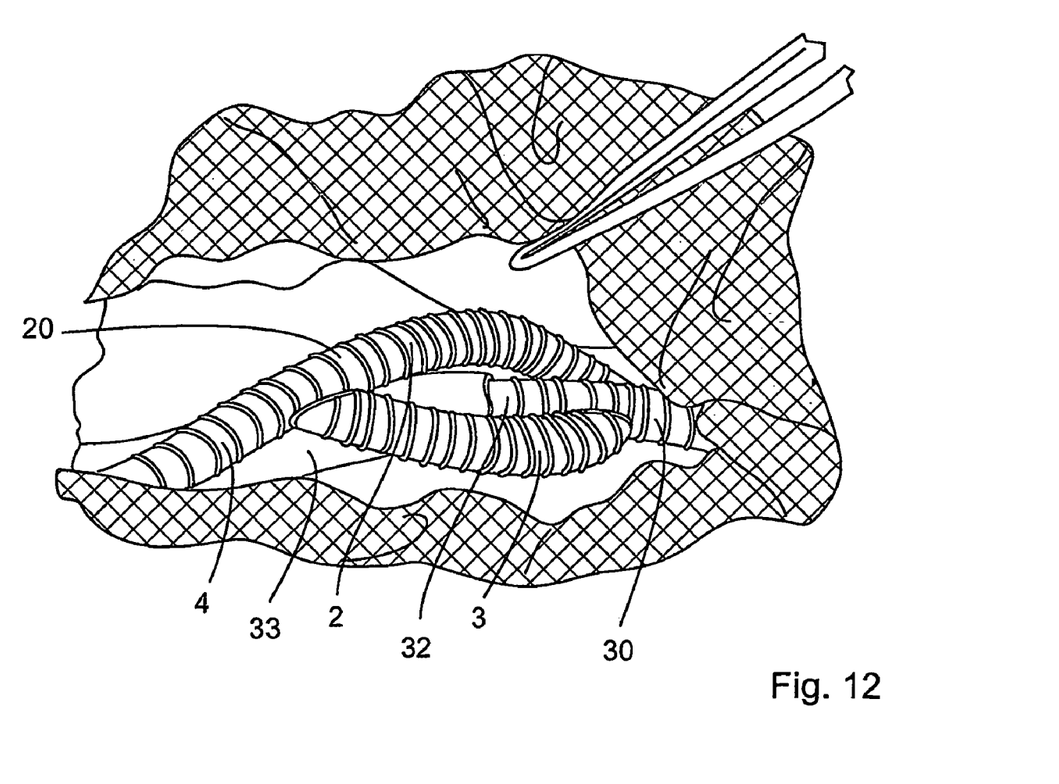
FIG. 12 is a photographic illustration of the graft of FIG. 11, in use.

Referring to FIGS. 11 and 12 there is illustrated another vascular graft 20 according to the invention, which is similar to graft 1 of FIGS. 4 to 10, and similar elements in FIGS. 11 and 12 are assigned the same reference numerals.

In this case the graft 20 comprises a distal flow conduit 30 for directing blood flow from the first branch 2 and from the second branch 3 to the second vasculature part 5.

The distal flow conduit 30 comprises means to attach a distal end 31 of the distal flow conduit 30 directly to a proximal end of the second vasculature part 5. The attachment is not at the sidewall of the second vasculature part 5, in this case. The attachment means may be provided in the form of sutures.

By attaching the distal end 31 to the proximal end of the second vasculature part 5, the difficulties, that may be experienced with the graft 1 of FIGS. 4 to 10 with gaining access to the side walls of the second vasculature part 5, may be avoided with the graft 20.

The distal flow conduit 30 also comprises means to attach a proximal end 32 of the distal flow conduit 30 directly to a distal end of a third vasculature part 33. The attachment means may be provided in the form of sutures.

The third vasculature part 33 and the second vasculature part 5 may be parts of the same vascular vessel. In such a case, the proximal end 32 of the distal flow conduit 30 is attached to an upstream part of a vascular vessel, and the distal end 31 of the distal flow conduit 30 is attached to a downstream part of the same vascular vessel in the form of two end-to-end anastomoses.

Alternatively the third vasculature part 33 and the second vasculature part 5 may be parts of different vascular vessels. In such a case, the proximal end 32 of the distal flow conduit 30 is attached to an upstream part of one vascular vessel, and the distal end 31 of the distal flow conduit 30 is attached to a downstream part of a different vascular vessel in the form of two end-to-end anastomoses.

The distal end of each branch 2, 3 is connected to a sidewall of the distal flow conduit 30. The two branches 2, 3 join to the distal flow conduit 30 in two inflow segments in a bifurcation arrangement. In this case the two branches 2, 3 are provided integral with the distal flow conduit 30 and with the proximal flow conduit 4.

The branches 2, 3 are connected to the distal flow conduit 30 with the distal openings 6, 7 arranged diametrically opposing one another, facing towards one another, and located at the same longitudinal region along the length of the distal flow conduit 30.

The distal flow conduit 30 extends distally of the region of connection of the branches 2, 3 to the distal flow conduit 30 by at least 5 mm, and extends proximally of this region of connection by at least 5 mm.

The anastomotic angle defined between each branch 2, 3 and the distal flow conduit 30 is in the range of from 15° to 60°, and the out-of-plane angle defined between each branch 2, 3 and the distal flow conduit 30 is in the range of from 5° to 45°.

It will be appreciated that the anastomotic angle defined between each branch 2, 3 and the distal flow conduit 30 may be chosen to suit the particular requirements. For example, the anastomotic angle may be 30° (FIG. 13), or 45° (FIG. 14), or 60° (FIG. 15).

The graft 20 comprises stiffening ribs around its circumference. The ribs are provided along the two branches 2, 3, the proximal flow conduit 4, and the distal flow conduit 30. To facilitate attachment of the ends 31, 32 of the distal flow conduit 30 to the second vasculature part 5 and to the third vasculature part 33 respectively, no ribs are provided adjacent the ends 31, 32 of the distal flow conduit 30.

It will be appreciated that the vascular graft of the invention may be formed from a variety of possible materials. The graft may be of a natural tissue material, such as harvested or grown vasculature materials. Alternatively the graft may be of an artificial biomaterial, such as Dacron or ePTFE. As a further alternative, the graft may be of a tissue engineered biomaterial.

In use, a proximal end of the proximal flow conduit 4 is attached to the first vasculature part, for example by means of suturing. The distal end 31 of the distal flow conduit 30 is attached directly to the proximal end of the second vasculature part 5, and the proximal end 32 of the distal flow conduit 30 is attached to the distal end of the third vasculature part 33 in the form of two end-to-end anastomoses.

In this manner, blood flow is directed from the first vasculature part into the proximal flow conduit 4, from the proximal flow conduit 4 into the first branch 2 and into the second branch 3, through the first branch 2 along the first flow path and through the second branch 3 along the second flow path, from the first branch 2 and from the second branch 3 into the distal flow conduit 30, and from the distal flow conduit 30 into the second vasculature part 5.

In the embodiment shown in FIG. 11, the opposing side branches 2, 3 are integral with the graft 20. The graft 20 comprises the distal end-to-end section 30 which is attached to the artery at two end-to-end anastomoses 31, 32. The branches 2, 3 are integral with the proximal primary section 4 of any desired length. In this embodiment the two joins are made by the surgeon at the spaced-apart end-to-end anastomoses 31, 32.

The anastomotic angle (the angle as viewed in FIG. 11 in the plane of the page between branches 2, 3 and distal section 30) is preferably in the range of 15° to 60°. The anastomotic angles of the two branches 2, 3 are not necessarily equal. The out-of-plane angle between the branches 2, 3 and the distal section 30 is preferably in the range of 5° to 45°.

The length of the distal section 30 is preferably at least 5 mm on each side beyond the junctions. This provides sufficient length for self-correction of flow within the graft 20.

The graft preferably has strengthening ribs around its circumference to avoid collapse and kinking. However, the distal section 30 is preferably free of such ribs adjacent its ends 31, 32, for ease of attachment to the host artery 5 by the surgeon.

The cross-sectional area of the distal section 30 may decrease towards its ends 31, 32, possibly in a tapered configuration. The diameter at the ends of the distal section 30 (FIG. 11 embodiment) or at the end of the branches 2, 3 (FIG. 4 embodiment) may be as low as 3 mm, for attachment to a narrow host artery.

Figure 13:
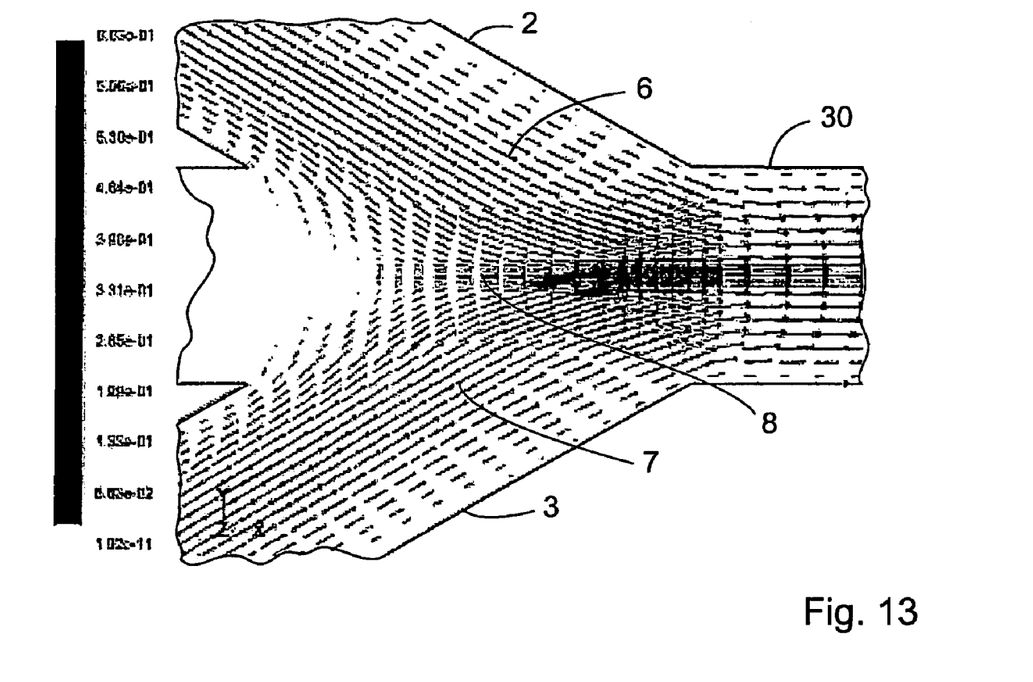
FIGS. 13 to 15 are cross-sectional, schematic illustrations of further vascular grafts according to the invention, in use.
Figure 14:
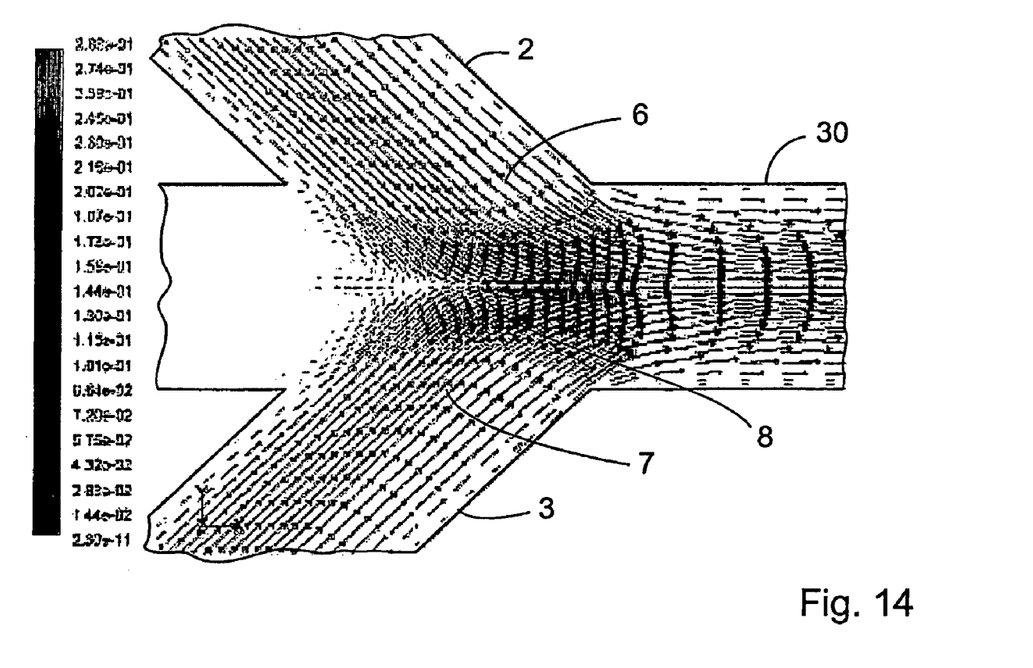
Figure 15:
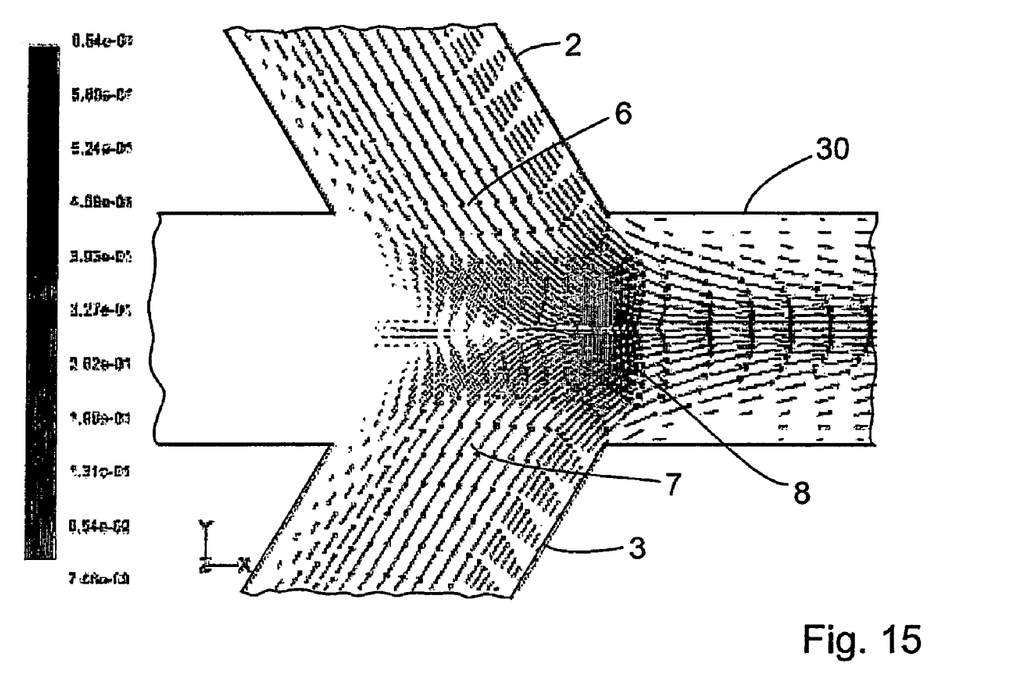

It will be appreciated from FIGS. 13 to 15 that the self-correcting flow pattern arises for a wide variety of anastomotic angles.

Referring to FIG. 10, the shear stresses are plotted for both the graft of the invention and for an anastomosis of the prior art. It is clear that the flow is non-laminar for a significantly longer length in the prior art. Also, in the prior art there is significant arterial bed impingement. In this illustration, the wall shear stress distributions represent the flow patterns present in the junction. To permit comparison, the diameters of all the conduits in both models are six millimeters. It is evident that the flow almost fully recovers within 2 diameters of the heel of the junction when the graft of the invention is used, compared to a flow recovery distance of greater than 5 diameters when a conventional graft is used. This reduction in flow recovery distance is believed to be a very positive characteristic of the graft of the invention returning the flow in the host artery to normal flow within a significantly reduced distance.

The graft of the invention could be made by a variety of methods and in various materials. For example, it could be made from harvested or grown vein materials. This may be done by a surgeon in the operating theatre. Alternatively, the graft could be made from currently proven biomaterials which are used in graft applications, such biomaterials including Dacron or ePTFE. The graft could be made from other tissue engineered biomaterials, which have not yet been fully developed but may become readily available over time.

The dimensions of the graft of the invention may be tailored to the application. It is expected that because the opposing junctions avoid the prior art problem of an arterial bed, smaller diameters may be achieved with an artificial graft of the invention. This is particularly advantageous for distal anastomoses, such as below the knee.

The following describes a surgical procedure using the graft:

The graft of the invention may be used as a conduit for bypass grafting of any occluded or stenosed artery, or as a conduit in the construction of an arteriovenous fistula for haemodialysis.

Typically the graft will be used in the operation of femoro-popliteal artery bypass. Under general or regional anaesthesia and following appropriate positioning and draping, the popliteal artery will be exposed either above or below the knee. Systemic heparin will be administered. The target artery will be divided and the distal graft-artery anastomoses constructed in an end-to-end fashion to both the distal and proximal cut ends of the target artery using an appropriately sized prolene suture (usually 6/0). The common, superficial and profunda femoral arteries will then be exposed in the groin. A tunnelling instrument will be passed from the groin incision subcutaneously to the popliteal incision and the proximal end of the graft will be brought through the tunnel to the groin where it will be anastomosed end-to-side to the femoral artery using a 5/0 or 6/0 prolene suture. The distal end may also be anastomosed to the tibial, peroneal or posterior tibial artery if indicated.

Figure 15A:
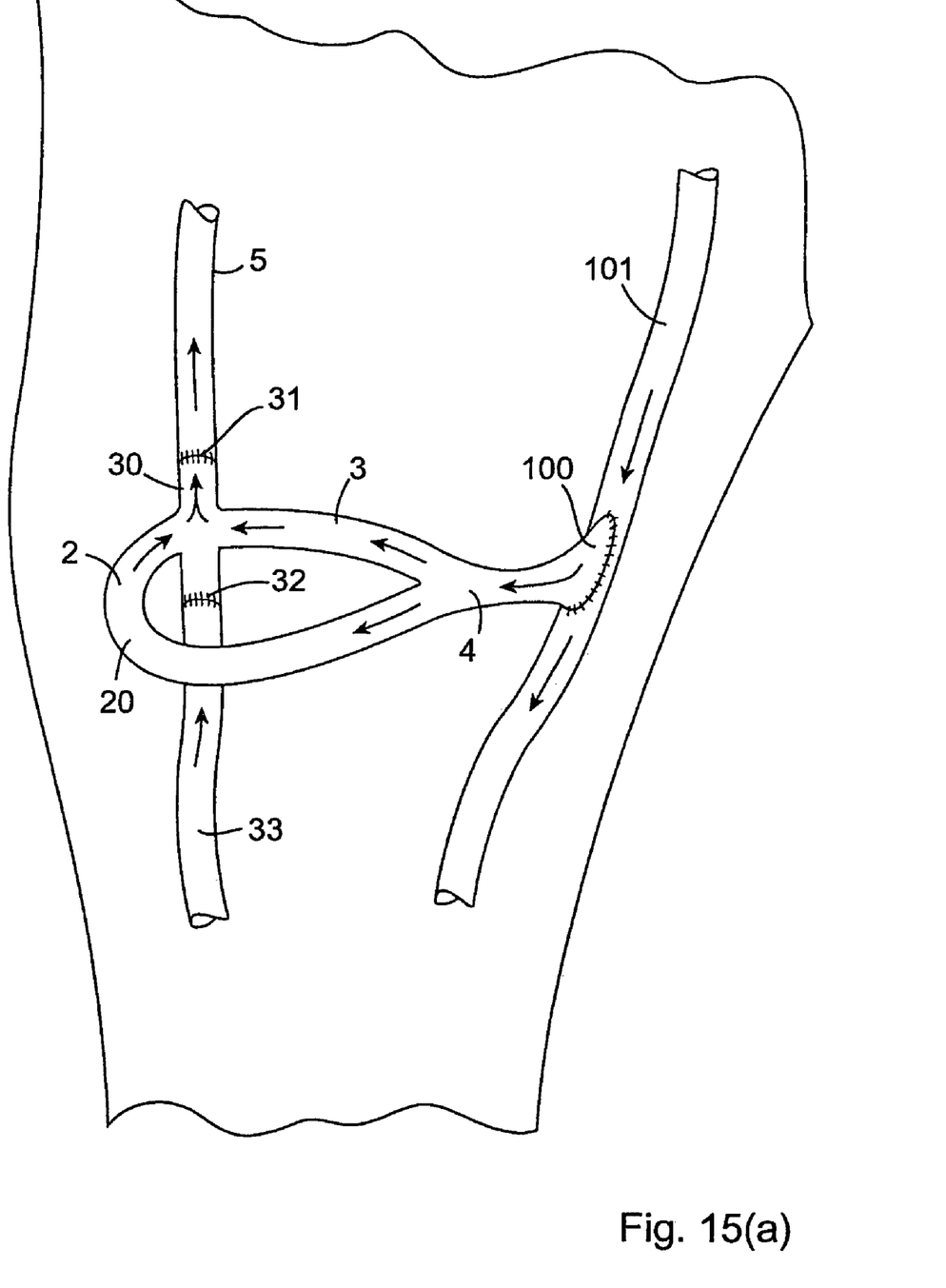

In one application, the graft 20 of the invention may be used to provide a clinically more effective solution to the introduction of flowing blood from the arterial system to the venous system (a so called A-V fistula). The graft 20 could, in the A-V fistula application, reduce fluid forces on the vein and improve long-term performance of the fistula. FIG. 15(*a*) illustrates the graft 20 in use during an A-V fistula application. The proximal end 100 of the proximal flow conduit 4 is directly attached to a side wall of the first vasculature part 101, which in this case is an artery. The third vasculature part 33 is an upstream part of a vein and the second vasculature part 5 is a downstream part of the same vein. In this case the proximal end 100 of the proximal flow conduit 4 is attached to the side wall of the first vasculature part 101 in the form of an end-to-side anastomosis. However it will be appreciated that the attachment may alternatively be provided in the form of an end-to-end anastomosis or in any other suitable form of attachment.

In another application, the graft of the invention could lead to an improved treatment of coronary artery blockages. This would be achieved by use of the unique geometrical and flow characteristics of the device in coronary bypass graft surgery (CABG). The device, with suitable modification may, be used in coronary vessels which have considerably smaller diameters than femoral arteries.

It will be appreciated from the diagrams of FIGS. 5 to 10 that the use of opposable junctions eliminates flow impinging on the artery bed, thus eliminating disease formation at this location. Also, the opposable junction geometry results in self-correcting flow, i.e. the flow patterns of the fluid as it enters the distal outflow segment are almost uniform and similar to what would have been present in a healthy artery pre-operatively.

Figure 16:
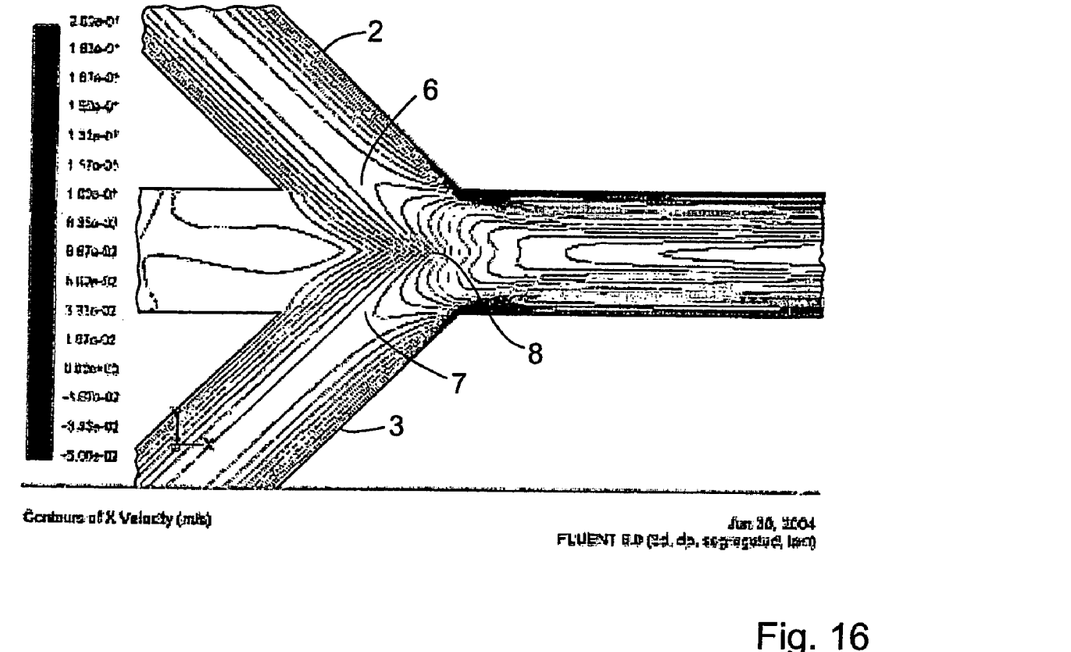
Figure 17:
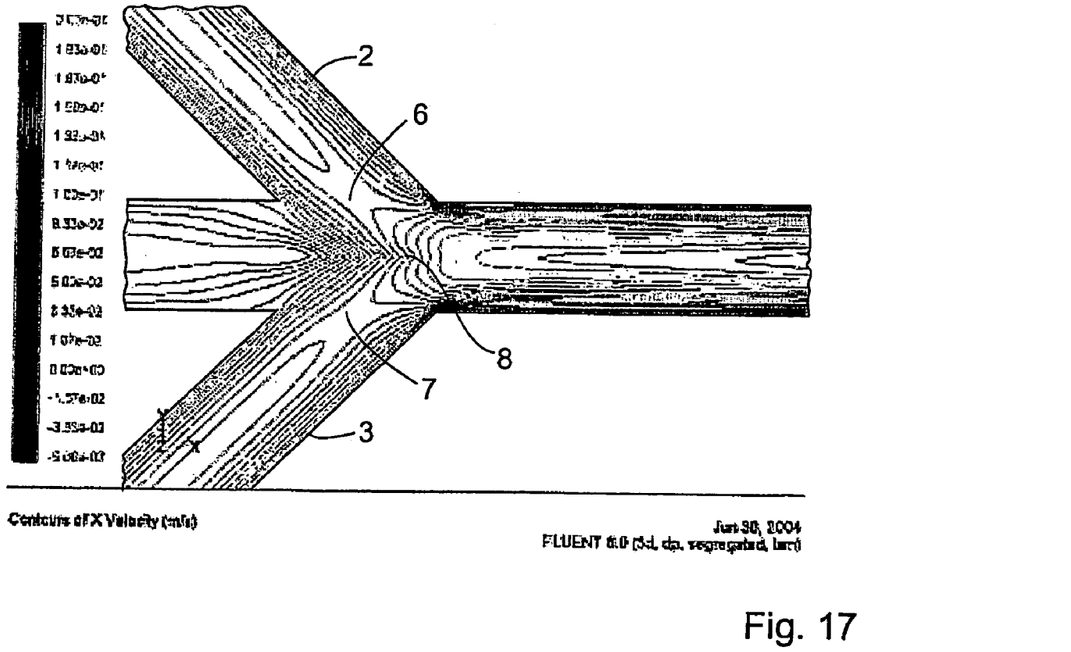

The invention in some uses avoids the need for a distal end-to-end anastomosis, allowing branched flow with "back flow" upstream towards an occlusion. Such back flow is very important in some uses as it allows blood feed to side arteries between an occlusion and an anastomosis. This aspect of the invention is illustrated in FIGS. 16 and 17. FIG. 16 illustrates the flow contours with zero back flow, and FIG. 17 illustrates the flow contours with 20% back flow.

The invention is not limited to the embodiments hereinbefore described, with reference to the accompanying drawings, which may be varied in construction and detail. For example, there may be more than two side branches. The proximal end of the primary section may also have branches, i.e. there are branches at both ends of the primary section.

The invention claimed is:

1. A vascular graft comprising:
   a first branch for directing flow between a first vasculature part and a second vasculature part along a first flow path;
   a second branch for directing flow between the first vasculature part and the second vasculature part along a second flow path,
   the first branch discharging flow to impinge upon flow being discharged out of the second branch;
   each branch including a distal opening through which flow is discharged out of the branch, and the distal opening of the first branch and the distal opening of the second branch being arranged opposing one another;
   the distal opening of the first branch facing towards the distal opening of the second branch;
   a distal flow conduit for directing flow from the first branch and from the second branch to the second vasculature part,
   the distal flow conduit including a distal attachment for attaching a distal end of the distal flow conduit directly to a proximal end of the second vasculature part,
   the distal opening of the first branch and the distal opening of the second branch being located at substantially a same longitudinal region along a length of the distal flow conduit;
   a distal end of the first branch and a distal end of the second branch being connected to a side wall of the distal flow conduit,
   the distal flow conduit including a proximal attachment for attaching a proximal end of the distal flow conduit to a third vasculature part,
   a proximal flow conduit for directing flow from the first vasculature part to the first branch and to the second branch,
   the proximal flow conduit including an attachment for attaching a proximal end of the proximal flow conduit to the first vasculature part, and
   the proximal end of the first branch and the second branch being connected to the proximal flow conduit in a bifurcation arrangement.

2. The graft as claimed in claim 1 wherein the distal opening of the first branch and the distal opening of the second branch are arranged diametrically opposing one another.

3. The graft as claimed in claim 1 wherein the anastomotic angle defined between the branch and the distal flow conduit is in the range of from 15° to 60°.

4. The graft as claimed in claim 1 wherein the out-of-plane angle defined between the branch and the distal flow conduit is in the range of from 5° to 45°.

5. The graft as claimed in claim 1 wherein the distal flow conduit extends distally of the distal end of the first branch and distally of the distal end of the second branch by at least 5 mm.

6. The graft as claimed in claim 1 wherein the distal flow conduit extends proximally of the distal end of the first branch and proximally of the distal end of the second branch by at least 5 mm.

7. The graft as claimed in claim 1 wherein the first branch and the second branch are integral with the distal flow conduit.

8. The graft as claimed in claim 1 wherein the first branch and the second branch are integral with the proximal flow conduit.

9. The graft as claimed in claim 1 wherein the graft comprises stiffening ribs around its circumference.

10. The graft as claimed in claim 9 wherein the ribs are not provided adjacent the distal end and/or adjacent the proximal end of the distal flow conduit.

11. The graft as claimed in claim 1 wherein the graft is at least partially of a natural tissue material.

12. The graft as claimed in claim 1 wherein the graft is at least partially of an artificial biomaterial.

13. The graft as claimed in claim 1 wherein the graft is at least partially of a tissue engineered biomaterial.

14. The graft as claimed in claim 1 wherein the first vasculature part is an upstream part of a vascular vessel, and the second vasculature part is a downstream part of the same vascular vessel.

15. The graft as claimed in claim 1 wherein the first vasculature part is an upstream part of a vascular vessel, and the second vasculature part in a downstream part of a different vascular vessel.

16. A method of performing a vascular bypass procedure using the vascular graft of claim 1, the method comprising the steps of:
   directing flow between a first vasculature part and a second vasculature part along a first flow path;
   directing flow between the first vasculature part and the second vasculature part along a second flow path,
   directing the flow between the first vasculature part and the second vasculature part along the first flow path through the first branch of the vasculature graft, and directing the flow between the first vasculature part and the second vasculature part along the second flow path through the second branch of the vascular graft, and the distal flow conduit is attached to the second vasculature part,
   attaching the proximal flow conduit to the first vasculature part, and
   attaching a proximal end of the distal flow conduit to a third vasculature part.

17. The method as claimed in claim 16 wherein the method comprises the step of forming the vascular graft at least partially from a natural tissue material.

18. The method as claimed in claim 16 wherein the method comprises the step of forming the vascular graft at least partially from an artificial biomaterial.

19. The method as claimed in claim 16 wherein the method comprises the step of forming the vascular graft at least partially from a tissue engineered biomaterial.

20. The method as claimed in claim 16 wherein the first vasculature part is an upstream part of a vascular vessel, and the second vasculature part is a downstream part of the same vascular vessel.

21. The method as claimed in claim 16 wherein the first vasculature part is an upstream part of a vascular vessel, and the second vasculature part is a downstream part of a different vascular vessel.

* * * * *

UNITED STATES PATENT AND TRADEMARK OFFICE
CERTIFICATE OF CORRECTION

PATENT NO. : 7,651,526 B2
APPLICATION NO. : 11/331275
DATED : January 26, 2010
INVENTOR(S) : Walsh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 879 days.

Signed and Sealed this

Twenty-third Day of November, 2010

David J. Kappos
*Director of the United States Patent and Trademark Office*